United States Patent

Okamoto et al.

[11] Patent Number: 5,202,433
[45] Date of Patent: Apr. 13, 1993

[54] POLYSACCHARIDE DERIVATIVES AS SEPARATING AGENTS

[75] Inventors: Yoshio Okamoto, Hyogo; Koichi Hatada, Osaka, both of Japan

[73] Assignee: Daicel Chemical Industries, Ltd., Sakai, Japan

[21] Appl. No.: 646,726

[22] PCT Filed: Jun. 7, 1990

[86] PCT No.: PCT/JP90/00743
§ 371 Date: Jan. 18, 1991
§ 102(e) Date: Jan. 18, 1991

[87] PCT Pub. No.: WO91/02006
PCT Pub. Date: Feb. 21, 1991

[30] Foreign Application Priority Data

Jul. 27, 1989 [JP] Japan .................. 1-194925

[51] Int. Cl.$^5$ .................. C07D 205/08; C07D 487/00
[52] U.S. Cl. .................. 540/200; 540/357; 540/362; 544/246; 549/401; 549/512; 568/336; 568/808; 568/730
[58] Field of Search .................. 536/4.1, 18.7, 20, 30, 536/31, 32, 51, 56, 58, 112, 102, 107, 115, 119, 1.1; 514/23, 53, 54, 55, 57, 60; 540/200, 357, 362; 544/246; 549/401, 512; 568/336, 174

[56] References Cited

U.S. PATENT DOCUMENTS

| | | | |
|---|---|---|---|
| 4,861,872 | 8/1989 | Okamoto et al. | 536/18.7 |
| 4,892,659 | 1/1990 | Shibata et al. | 536/119 |
| 4,912,094 | 3/1990 | Myers et al. | 536/119 |
| 4,912,205 | 3/1990 | Okamoto et al. | 536/20 |
| 4,976,952 | 12/1990 | Lang et al. | 536/20 |
| 5,041,226 | 8/1991 | Shibata et al. | 536/119 |

FOREIGN PATENT DOCUMENTS

| | | |
|---|---|---|
| 60-142930 | 7/1985 | Japan . |
| 60-217201 | 10/1985 | Japan . |
| 60-223802 | 11/1985 | Japan . |
| 61-233633 | 10/1986 | Japan . |
| 61-254604 | 11/1986 | Japan . |
| 62-64801 | 3/1987 | Japan . |
| 62-135450 | 6/1987 | Japan . |
| 63-178101 | 7/1988 | Japan . |

Primary Examiner—Johnnie R. Brown
Assistant Examiner—Everett White
Attorney, Agent, or Firm—Flynn, Thiel, Boutell & Tanis

[57] ABSTRACT

A polysaccharide derivative prepared by replacing a part or the whole of hydrogen atoms of hydroxyl and/or amino groups of a polysaccharide with one or more atomic groups represented by the following formula (1), (2) or (3) is new and useful for the separation of optical isomers:

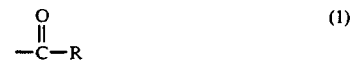

(1)

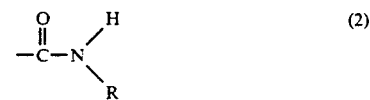

(2)

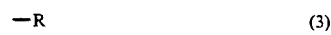

(3)

wherein the number of carbon atoms constituting R is 1 to 30 and R is a group having at least one asymmetric center.

8 Claims, No Drawings

POLYSACCHARIDE DERIVATIVES AS SEPARATING AGENTS

TECHNICAL FIELD

The present invention relates to a new polysaccharide derivative which is extremely useful as a functional material for optical resolution. Particularly, the present invention relates to a new polysaccharide derivative having an asymmetric carbon atom group, and a separating agent comprising said polysaccharide derivative. Further, the present invention relates to a process for the separation of β-lactam stereoisomers.

BACKGROUND ART

Derivatives prepared by reacting polysaccharides with achiral compounds are known. These derivatives have a structure wherein an achiral group is bonded to a stereoregular polymer chain, so that they can discriminate the asymmetry of various racemic modifications when used as column packings for liquid chromatography. However, they are apt to fail in discriminating the asymmetry of some racemic modifications of compounds having complicated structures such as those having two asymmetric centers in the same molecule or those having various functional groups in their asymmetric centers.

The present invention aims at providing a polysaccharide derivative and a separating agent having a higher asymmetry discriminating power, which are prepared by reacting a polysaccharide with a chiral compound to thereby regulate the configurations of both the backbone chain and the side chain.

β-Lactams are important substances as raw materials for the preparation of various drugs including antibiotics. The separation of a β-lactam into respective stereoisomers is essential because the action of such a drug on a living organism is, in many cases, different depending upon the kind of stereoisomer used in the preparation thereof, like in the case of thalidomide [see G. Blaschke, Angew. Chem. Int. Ed. Engl., 19, 13 (1980)].

Known processes for preparing a β-lactam stereoisomer include asymmetric synthesis, diastereomer process and chromatographic process. Among these processes, the chromatographic process has advantages in that a high-purity stereoisomer can be obtained and continuous operation because possible by employing Sorbex techniques. However, none of the columns which have been used for the separation of β-lactam stereoisomers exhibit a sufficiently high separating power and, therefore, the separation of same β-lactams has been impossible as yet.

DISCLOSURE OF INVENTION

Under these circumstances, the present invention relates to a new polysaccharide derivative prepared by replacing some or all of the hydrogen atoms of the hydroxyl and/or amino groups of a polysaccharide with one or more atomic groups represented by the following formula (1), (2) or (3), and to a separating agent comprising said polysaccharide derivative as the main component:

$$-\overset{O}{\underset{\|}{C}}-R \qquad (1)$$

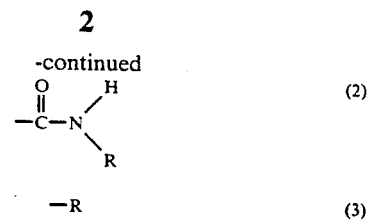

−R (3)

wherein the number of carbon atoms constituting R is 1 to 30 and R is a group having at least one asymmetric carbon atom.

The degree of replacement with the above atomic groups is at least 30%, preferably at least 50%, still preferably at least 85%.

It has now been found that β-lactams can be efficiently separated into respective stereoisomers by using a separating agent comprising the above polysaccharide derivative as the main component.

The polysaccharide derivative of the present invention has a chiral side chain and can resolve a racemic mixture. The resolving power of the derivative can be exhibited not only by itself but also when it is supported on a carrier.

The present invention also provides a process for separating a racemic mixture, particularly a compound represented by the following general formula (4), into respective stereoisomers by using a separating agent comprising the above polysaccharide derivative as the main component:

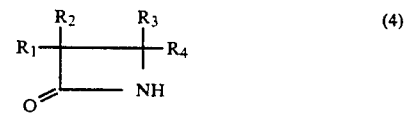

wherein $R_1$, $R_2$, $R_3$ and $R_4$ are each a hydrogen atom or a substituent having 1 to 30 carbon atoms, with the proviso that if $R_1$ and $R_2$ are the same, $R_3$ and $R_4$ are different from each other and if $R_3$ and $R_4$ are the same, $R_1$ and $R_2$ are different from each other.

In the above general formula (4), $R_1$, $R_2$, $R_3$ and $R_4$ are each a group wherein all of the constituent carbon atoms are of $sp^3$ hybrid orbital (an atomic orbital of a carbon atom of a C—C single bond) or a group constituted of carbon atoms of two or three hybrid orbitals selected from among $sp^3$, $sp^2$ (an atomic orbital of a carbon atom of a C=C double bond) and sp (an atomic orbital of a carbon atom of a C≡C or C≡N triple bond) and may contain atoms other than oxygen, nitrogen and carbon. Geometrically, $R_1$, $R_2$, $R_3$ and $R_4$ may be linear or cyclic and straight-chain or branched. Particular examples thereof include the following:

A) groups wherein the constituent carbon atoms are all $sp^3$ hybridized.
(1) $R_1$, $R_2$, $R_3$, and $R_4$:

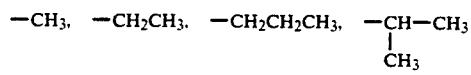

B) groups comprising $sp^3$ hybridized carbon atom and $sp^2$ hybridized carbon atom.
(1) $R_1$, $R_2$, $R_3$, and $R_4$:

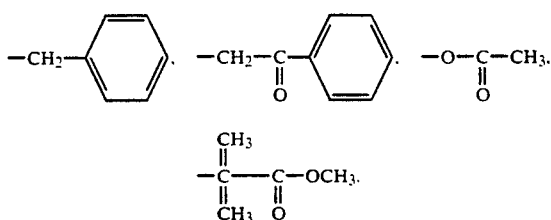

C) groups comprising sp³ hybridized carbon atom and sp hybridized carbon atom.

(1) $R_1$, $R_2$, $R_3$, and $R_4$:

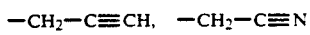

The β-lactams described above can be efficiently separated into stereoisomers by using a separating agent comprising the inventive polysaccharide derivative.

Although the polysaccharide according to the present invention may be any of synthetic, natural and modified natural ones, as far as it is optically active, it is preferable that the polysaccharide have high regularity in its bonding. Examples thereof include α-1,4-glucan (such as amylose and amylopectin), α-1,6-glucan (such as dextran), β-1,6-glucan (such as pustulan), β-1,3-glucan (such as curdlan and schizophyllan), α-1,3-glucan, β-1,2-glucan (such as Crown Gall polysaccharide), β-1,4-galactan, β-1,4-mannan, α-1,6-mannan, β-1,2-fructan (such as inulin), β-2,6-fructan (such as levan), β-1,4-xylan, β-1,3-xylan, β-1,4-chitosan, β-1,4-N-acetylchitosan (such as chitin), pullulan, agarose, alginic acid and amylose-containing starches, among which amylose, β-1,4-chitosan, chitin, β-1,4-mannan, β-1,4-xylan, inulin and curdlan are particularly preferable, because high-purity polysaccharides can be easily obtained therefrom.

From the standpoint of handleability, the number-average degree of polymerization of the polysaccharide (average number of pyranose or furanose rings contained in one molecule) is 5 or above, preferably 10 or above and the upper limit thereof is 2000, preferably 500.

The atomic group to be introduced into the polysaccharide is one derived from a compound which reacts with a hydroxyl or amino group of the polysaccharide to form an ester, urethane (carbamate) or ether linkage and is represented by the formula (1), (2) or (3).

The number of carbon atoms constituting R in the formulas (1) to (3) is from 1 to 30 and R has at least one asymmetric carbon atom. Further, R may contain a functional group which is inert to practical reactions, for example, an ether or carbonyl linkage or a halogen atom. Further, R can be a group comprising carbon atoms only of sp³ hybrid orbital (an atomic orbital of a carbon atoms having a C—C single bond) or a group comprising carbon atoms of two or three hybrid orbitals selected from among sp³, sp² (an atomic orbital of a carbon atom having a C=C double bond) and sp (at atomic orbital of a carbon atom having a C≡C or C=C triple bond) and geometrically, it may be either linear or cyclic. Particular examples thereof include the groups which will be described below.

In the following formulas, the symbol "*" represents an asymmetric carbon atoms.

A) groups wherein the constituent carbon atoms are all sp³ hybridized.

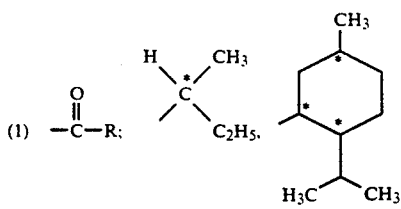

B) groups comprising sp³ hybridized carbon atom(s) and sp² hybridized carbon atom(s).

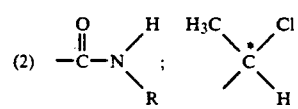

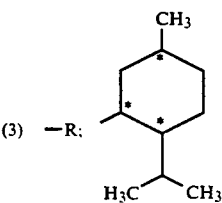

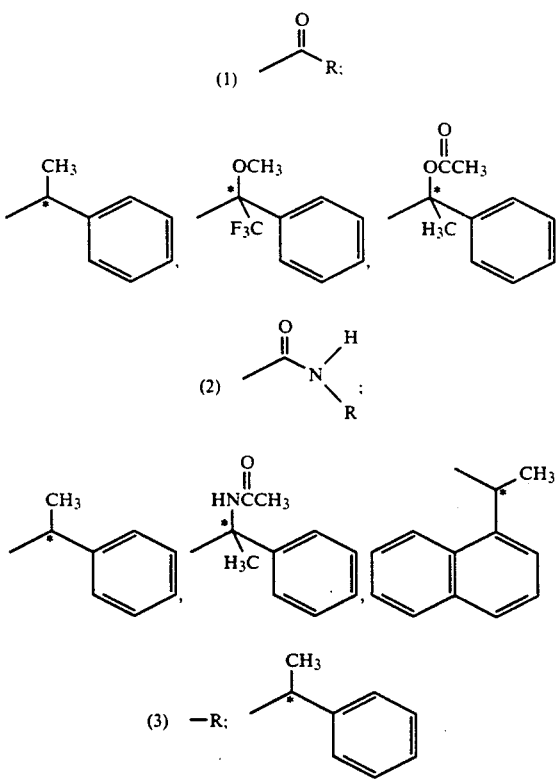

According to the present invention, one or more of the atomic groups of the formulas (1), (2) and (3) may be introduced into a polysaccharide. It is preferable to select the atomic groups to be introduced depending upon the objective separation performance.

Further, R may be a molecular-asymmetrical group and examples thereof include the following:

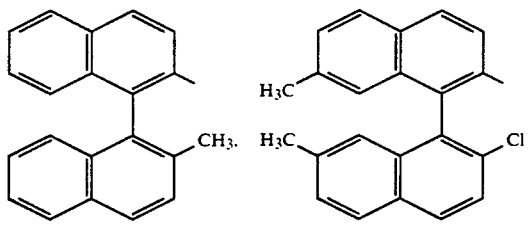

The polysaccharide derivative of the present invention can be prepared by, for example, the following processes:

1) ester linkage

The carbonyl group constituting the polysaccharide ester derivative according to the present invention is represented by the above general formula (1) and the carbonyl group forms ester linkages together with 30 to 100%, preferably at least 50%, still more preferably at least 85% of the total hydroxyl and/or amino groups of the polysaccharide.

The ester derivative according to the present invention can be easily prepared by reacting the corresponding carboxylic acid with thionyl chloride, oxalyl chloride or the like to give an acid chloride and reacting the acid chloride with the corresponding polysaccharide in pyridine as a solvent.

2) carbamate linkage

The carbamoyl group constituting the polysaccharide carbamate derivative according to the present invention is represented by the above general formula (2) and forms urethane linkages together with 30 to 100%, preferably at least 50%, still more preferably at least 85% of the total hydroxyl and/or amino groups of the corresponding polysaccharide.

The carbamate derivative according to the present invention can be prepared by a conventional process for preparing a urethane from an alcohol and an isocyanate. For example, the carbamate derivative can be prepared by reacting the corresponding isocyanate with the corresponding polysaccharide in a suitable solvent in the presence of a Lewis base such as a tertiary amine or a Lewis acid such as a tin compound as a catalyst. The isocyanate to be used above can be easily prepared by reacting the amino group of the corresponding aniline derivative with phosgene.

3) ether linkage

The group constituting the polysaccharide ether derivative according to the present invention is represented by the above general formula (3) and forms ether linkages together with 30 to 100%, preferably at least 50%, still more preferably at least 85% of the total hydroxyl and/or amino groups of the corresponding polysaccharide.

The ether derivative according to the present invention can be prepared by reacting the corresponding halide with the corresponding polysaccharide in dioxane or pyridine in the presence of a base such as potassium hydroxide or potassium t-butoxide.

In the use of the polysaccharide derivative according to the present invention as a separating agent for liquid chromatography, it is convenient to pack the derivative in a powdered state into a column. Therefore, the polysaccharide derivative is preferably pulverized or formed into a bead and the resulting particle is still preferably porous. Further, it is preferable to support the polysaccharide derivative on a carrier with the purpose of improving the pressure resistance of the separating agent, preventing the agent from swelling and shrinking due to solvent replacement and enhancing the theoretical plate number.

Although the particle size of the powdered polysaccharide derivative and the size of the carrier vary depending upon the size of the column used, they range from 1 μm to 1 mm, preferably from 1 μm to 300 μm. The carrier is preferably a porous one and the mean pore size thereof ranges from 10 Å to 100 μm, preferably from 50 Å to 50000 Å. The amount of the polysaccharide derivative to be supported on a carrier is 1 to 100% by weight, preferably 5 to 50% by weight based on the carrier.

The process for making the polysaccharide derivative supported on a carrier may be either a chemical one or a physical one. The physical process includes a process which comprises mixing a solution of the polysaccharide derivative in a solvent with a carrier and distilling the mixture with an air stream either under a reduced pressure or at an elevated temperature to remove the solvent, and a process which comprises mixing a solution of the derivative in a solvent with a carrier and diffusing the solvent with a non-solvent for the derivative. The separating agent thus prepared may be subjected to a suitable treatment such as heating, addition of a solvent or washing in order to improve the separating power thereof.

The carrier to be used in the present invention includes porous organic carriers and porous inorganic carriers, among which the latter are preferable. Suitable examples of the porous organic carrier include polymers such as polystyrene, polyacrylamide and polyacrylate. Suitable examples of the porous inorganic carrier include silica, alumina, magnesia, glass, kaolin, titanium oxide and silicates. The surface of such a porous inorganic carrier may be treated in order to improve the affinity of the carrier with the carbamate derivative or the surface characteristics thereof. The surface treatment includes silylation with an organosilane compound and plasma polymerization.

The developer to be used in the liquid chromatography using the polysaccharide derivative of the present invention is not particularly limited with the proviso that those in which the derivative is soluble and those which are reactive with the derivative are excluded. When the polysaccharide derivative is chemically supported on a carrier or insolubilized by crosslinking, the developer may be any one except those which are reactive with the derivative.

The polysaccharide derivative of the present invention is extremely useful as a functional material, particularly as a packing for optical resolution, i.e., separating agent.

Although the separation of a mixture of compounds or an optical isomer mixture with the polysaccharide derivative of the present invention is generally conducted by gas, liquid or thin layer chromatography using a column packed with the polysaccharide derivative, it may be conducted by membrane separation techniques using a membrane containing the polysaccharide derivative.

In the application of the polysaccharide derivative to thin-layer chromatography, a layer comprising the derivative in the form of a particle having a size of 0.1 μm to 0.1 mm and, if necessary, a small amount of a binder having a thickness of 0.1 to 100 mm is formed on a support.

In the application of the polysaccharide derivative to membrane separation, the derivative is used in the form of a hollow yarn or a film.

EXAMPLE

The present invention will now be described in more detail by referring to the following Examples, though the present invention is not limited to them. Further, the separation effect of the polysaccharide derivative will be also illustrated in the following Application Examples.

EXAMPLE 1 synthesis of cellulose tris(1-phenylethylcarbamate)

0.80 g of cellulose (Avicel, a product of Merck) was stirred in a mixture comprising 1.2 g of LiCl and 12 ml of N,N-dimethylacetamide at 80° C. for 6 hours. 6 ml of pyridine and 3.5 ml of (−)-1-phenylethyl isocyanate were added thereto to carry out a reaction at 100° C. for 26 hours. The reaction mixture was poured into methanol to precipitate a product. This product was recovered by filtration through a glass filter and dried in a vacuum at 60° C.

amount of the product: 2.21 g, yield: 74.2%

The (−)-1-phenylethyl isocyanate used above was prepared by reacting (−)-1-phenylethylamine with phosgene.

(−)-1-phenylethyl isocyanate: b.p.: 69° to 71° C./ 6 mmHg

The results of the elemental analysis of the obtained cellulose tricarbamate derivative (hereinafter referred to as "(−)-isomer") are as follows:

|  | C % | H % | N % |
|---|---|---|---|
| found: | 64.42 | 6.08 | 6.78 |
| calculated: | 65.66 | 6.18 | 6.96 |

APPLICATION EXAMPLE 1

One part (by weight, the same applies hereinbelow) of the polysaccharide derivative prepared in Example 1 was dissolved in 8 parts of acetone to give a solution. This solution was mixed with 4 parts of diphenylsilane-treated silica gel (a product of Merck, Lichrospher Si-1000). The acetone was removed from the resulting mixture by vacuum distillation to give a separating agent, which was packed into a stainless steel column having an inner diameter of 0.46 cm and a length of 25 cm by a slurry method using methanol.

Various racemic mixtures were separated by using the resulting packed column. The results are given in Table 1.

The capacity ratio (k'), separation factor (α) and resolution (Rs) given in the Table are those defined by the following equations, respectively:

$$\text{capacity ratio } (k') = \frac{\text{retention time of separated compound} - \text{dead time}}{\text{dead time}}$$

$$\text{separation factor } (\alpha) = \frac{\text{capacity ratio of more strongly adsorbed compound}}{\text{capacity ratio of more weakly adsorbed compound}}$$

$$\text{resolution } (Rs) = \frac{2 \times \begin{pmatrix} \text{distance between the peak of more} \\ \text{strongly adsorbed compound and that} \\ \text{of more weakly adsorbed compound} \end{pmatrix}}{\text{sum total of half-widths of both peaks}}$$

(A resolution of 1 or above means complete separation)

TABLE 1

| Racemic mixture | (−)-isomer | | |
|---|---|---|---|
|  | $k_1'$ | α | Rs |
| trigger base | 0.45 (−) | ~1 |  |
| (Ph-O-Ph epoxide structure) | 0.37 (−) | ~1 |  |
| (cyclopropane-CONHPh, Ph) | 3.58 | ~1 |  |
| benzoin | 2.24 (+) | 1.16 | 1.20 |
| Co(acac)₃ | 0.50 (+) | 1.19 |  |
| (anthracene-OH-CH-CF₃) | 2.03 (−) | 1.28 | 1.34 |

Note) eluent: hexane/2-propanol = 90/10 (by volume)

EXAMPLE 2 synthesis of xylan bis((+)-1-phenylethylcarbamate) and xylan bis((−)-1-phenylethylcarbamate)

1) synthesis of (+) and (−)-1-phenylethyl isocyanates

The synthesis was carried out according to a conventional process.

−(+)-1-phenylethyl isocyanate
66.2° to 67.8° C./5 mmHg
yield: 69.4%
$[\alpha]_D^{25}$: +10.4°
(Aldrich $[\alpha]^{19}$: +9.2° (neat))
(−)-1-phenylethyl isocyanate
66.3° to 66.8° C./5 mmHg
yield: 71.1%

2) synthesis of xylan bis(1-phenylethylcarbamate)

A reflux condenser was set on a 50-ml two-necked flask. 0.80 g of xylan (a product of Seikagaku Kogyo K.K.) and 0.85 g of LiCl were fed into the flask in a nitrogen atmosphere, followed by the addition of 6 ml of dry dimethylacetamide (on a molecular sieve). The obtained mixture was stirred at 90° C. for 2 hours to give a homogeneous system having a considerably high viscosity. 15 ml of dry pyridine (on KOH) was added to the flask, followed by the addition of 2.5 ml (molar amount of OH group of the xylan x 1.5) of 1-phenylethyl isocyanate. After 24 hours, no isocyanate was present in the reaction mixture (as analyzed by IR) and the reaction had proceeded only a little. Therefore, 1.1 ml of 1-phenylethyl isocyanate was further added to the flask. After 92 hours from the initiation of the reaction, the reaction mixture was poured into methanol to give a precipitate. This precipitate was recovered by centrifuging. Just before the recovery, the isocyanate remained in the reaction system (as analyzed by IR). The steps subsequent to the above addition of the pyridine were conducted in a state wherein a calcium chloride tube was set on the flask.

The obtained xylan bis((+)-1-phenylethylcarbamate) (hereinafter referred to as "(+)-isomer") and xylan bis((−)-1-phenylethylcarbamate) (hereinafter referred to as "(−)-isomer") each have a structure represented by the following formula:

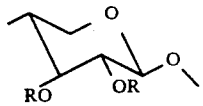

R = —CONH—C*—H
         |
         CH₃

| | | (+)-isocyanate | (−)-isocyanate |
|---|---|---|---|
| Yield (%) | | 42.6 | 59.4 |
| Elemental analysis | C % | 64.28 (64.79) | 64.49 |
| | H % | 6.20 (6.10) | 6.23 |

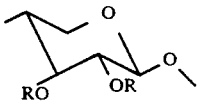

R = —CONH—C*—H
         |
         CH₃

| | (+)-isocyanate | (−)-isocyanate |
|---|---|---|
| N % | 6.60 (6.57) | 7.02 |

Note) figures in parentheses are calculated values

Application Example 2

0.75 g of the xylan bis(1-phenylethylcarbamate) prepared in Example 2 was dissolved in 7 ml of dimethylacetamide to give a solution. This solution was mixed in two or three portions with 3 g of silica gel (4000-7, treated with 3-aminopropyltriethyoxysilane) to support the xylan bis(1-phenylethylcarbamate) on the silica gel. The separating agent thus obtained was packed into a column (25×0.46 (i.d.) cm) dispersed in a hexane/liquid paraffin (2:1) mixture.

pressure : 330 kg/cm²

Various racemic mixtures were separated by using the resulting packed column. The results are given in Tables 2, 3 and 4.

TABLE 2

| Racemic mixture | (+)-isomer | | | (−)-isomer | | |
|---|---|---|---|---|---|---|
| | k₁' | α | Rs | k₁' | α | Rs |
| 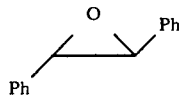 | 0.58(+) | 1.14 | | 0.89(+) | 1.10 | |
| 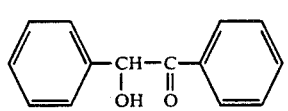 | 5.46(+) | 1.07 | | 3.44(+) | 1.26 | 1.70 |
| 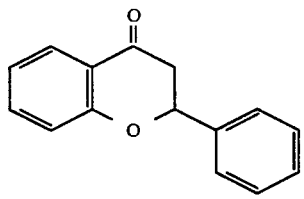 | 1.92(+) | ~1 | | 1.64(−) | 1.27 | 1.74 |
| 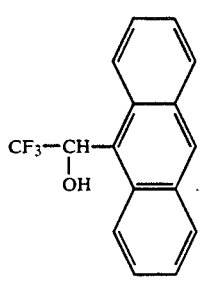 | 3.40 | 1.00 | | 3.00(−) | 1.82 | 3.03 |

TABLE 2-continued

| Racemic mixture | (+)-isomer $k_1'$ | $\alpha$ | Rs | (−)-isomer $k_1'$ | $\alpha$ | Rs |
|---|---|---|---|---|---|---|
| 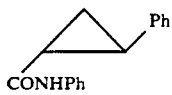 | 8.04(−) | 1.09 | | 8.04(+) | 1.23 | 1.41 |
| 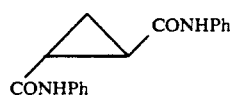 | ~4.4 | 1.00 | | 2.29(+) | 1.44 | |

Note) The eluent used in Tables 2, 3 and 4 is a hexane/2-propanol (90/10, by volume) mixture, with the proviso that the eluent used in the cases marked with a symbol "b)" is a hexane/2-propanol (98/2, by volume) mixture.

TABLE 3

| Racemic mixture | (+)-isomer $k_1'$ | $\alpha$ | Rs | (−)-isomer $k_1'$ | $\alpha$ | Rs |
|---|---|---|---|---|---|---|
| 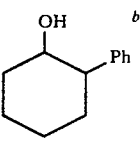 b) | 1.36(+) | ~1 | | 1.46(+) | 1.15 | 0.91 |
| 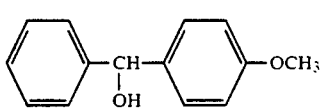 | 2.60 | 1.00 | | 4.08(−) | 1.10 | |
| 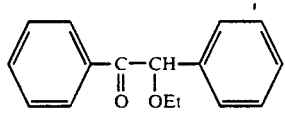 | 1.25(−) | 1.17 | 0.79 | 1.89(−) | ~1 | |
| 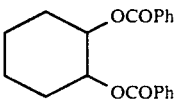 | 2.39(−) | ~1 | | 2.04(+) | 1.16 | 0.66 |

TABLE 4

| Racemic mixture | (+)-isomer $k_1'$ | $\alpha$ | Rs | (−)-isomer $k_1'$ | $\alpha$ | Rs |
|---|---|---|---|---|---|---|
| 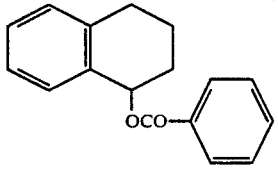 b) | 0.80(+) | ~1 | | 0.84(−) | 1.19 | 0.71 |
| 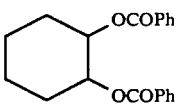 b) | 2.39(−) | ~1 | | 2.04(+) | 1.16 | 0.66 |
| 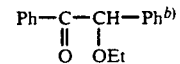 b) | 1.25(−) | 1.17 | 0.79 | 1.89(−) | ~1 | |

EXAMPLE 3 synthesis of amylose tris ((−)-1-phenylethylcarbamate

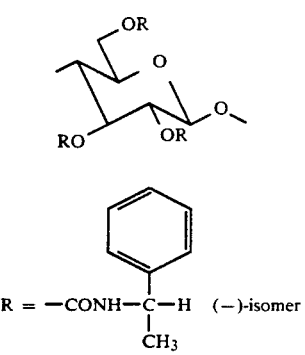

R = —CONH—C—H (−)-isomer
           |
           CH₃

A reflux condenser was set on a 50-ml two-necked flask. 0.80 g of amylose (Nakarai Chemicals) and 0.80 g of LiCl were fed into the flask in a nitrogen atmosphere, followed by the addition of 5 ml of dry dimethylacetamide (on a molecular sieve). The contents were stirred under heating at 90° C. for 2 hours to give a heterogeneous system. 7 ml of dry pyridine (on KOH) was added to the flask, followed by the addition of (−)-1-phenylethyl isocyanate. The obtained mixture was kept at 90° C. for 50 hours to carry out a reaction. The resulting reaction system had a considerably high viscosity. When the reaction mixture was poured into methanol, the formed polymer precipitated in the form of not a powder but a thread.

amount of the product: 1.33 g, yield: 44.7%

The polymer was subjected to solvent fractionation with THF.

solubles; 0.77 g (61.1%)

insolubles; 0.49 g (38.9%) unreacted OH groups were recognized

The amount of the obtained amylose tris((−)-1-phenyl-ethylcarbamate) was 0.77 g and the yield thereof was 25.9%.

| elemental analysis | C % | H % | N % |
|---|---|---|---|
| found: | 63.93 | 6.05 | 6.72 |
| calculated: | 65.72 | 6.14 | 6.97 |

APPLICATION EXAMPLE 3

0.72 g of the polymer prepared in Example 3 was dissolved in 15 ml of THF and supported on 2.90 g of silica gel (treated with 3-aminopropyltriethoxysilane). The separating agent thus obtained was packed into a column in a state dispersed in a hexane/liquid paraffin (2:1) mixture and pressed at 330 kg/cm².

Various racemic mixtures were optically resolved by using the resulting packed column. The results are given in Table 5.

EXAMPLE 4 synthesis of amylose tris((+)-1-phenylethylcarbamate

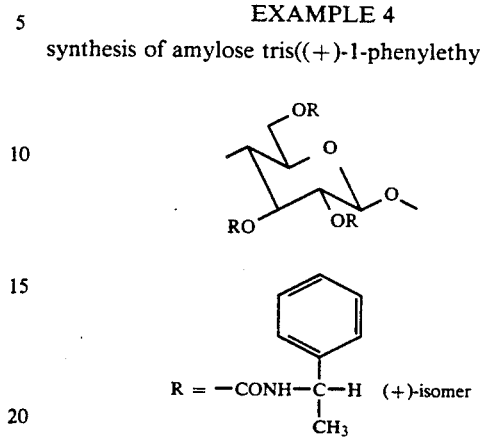

R = —CONH—C—H (+)-isomer
           |
           CH₃

A reflux condenser was set on a 50-ml two-necked flask. 0.80 g of amylose (Nakarai Chemicals) and 0.80 g of LiCl were fed into the flask, followed by the addition of 7 ml of dry dimethylacetamide (on a molecular sieve). The contents were stirred under heating at 90° C. for 5 hours to give a heterogeneous system. 10 ml of dry pyridine (on KOH) was added to the flask, followed by the addition of 3.6 g of (+)-1-phenylethyl isocyanate. The contents were kept at 90° C. for 70 hours to carry out a reaction. The resulting reaction mixture had a considerably high viscosity. When the reaction mixture was poured into methanol, the formed polymer precipitated in the form of not a powder but a thread.

The polymer was subjected to solvent fractionation with THF.

solubles: 0.72 g (61.1%)

The amount of the obtained amylose tris((+)-1-phenylethylcarbamate) was 0.72 g and the yield thereof was 22.6%.

| elemental analysis | C % | H % | N % |
|---|---|---|---|
| found: | 64.85 | 6.11 | 6.87 |
| calculated: | 65.72 | 6.14 | 6.97 |

APPLICATION EXAMPLE 4

0.72 g of the polymer prepared in Example 4 was dissolved in 15 ml of THF and supported on 2.90 g of silica gel (treated with 3-aminopropyltriethoxysilane). The obtained separating agent was packed into a column dispersed in a hexane/liquid paraffin (2:1) mixture and pressed at 330 kg/cm².

Various racemic mixtures were optically resolved by using the packed column. The results are given in Table 5.

TABLE 5

| Racemic mixture | (+)-isomer | | | (−)-isomer | | |
|---|---|---|---|---|---|---|
| | k₁' | α | Rs | k₁' | α | Rs |
| 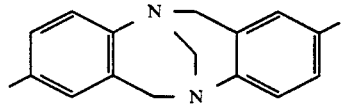 | 0.74 | 1.86 | 2.41 | 0.90(+) | 2.38 | 4.43 |

TABLE 5-continued
| Racemic mixture | (+)-isomer | | | (−)-isomer | | |
|---|---|---|---|---|---|---|
| | $k_1'$ | α | Rs | $k_1'$ | α | Rs |
| 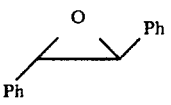 | 0.61 | 1.19 | 0.83 | 0.61(+) | 1.28 | 1.52 |
| 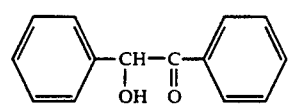 | 3.73 | 1.14 | 1.29 | 4.29(+) | 1.98 | 9.10 |
| 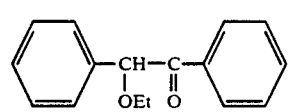 | 0.78 | 1.49 | 2.16 | 0.72 | 1.48 | 2.34 |
| 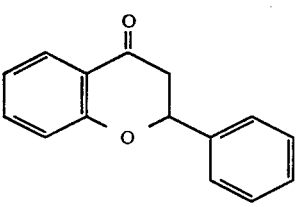 | 2.07 | 1.07 | | 3.02 | ~1 | |
| 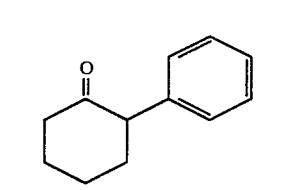 | 1.10(−) | ~1 | | 1.50(+) | 1.21 | 1.68 |
|  | 1.97(+) | 1.05 | | 1.95(−) | 1.88 | 5.67 |
| 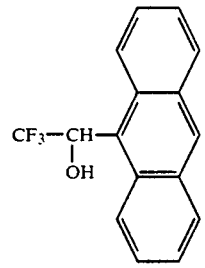 | 4.46(+) | 1.18 | 1.01 | 4.79(+) | 1.19 | 1.67 |
|  | | | | 4.06(+) | 1.34 | 1.33 |
| 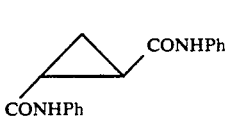 | 1.27(−) | 1.10 | | 1.11(−) | 2.03 | 4.99 |
| 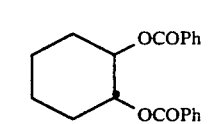 | 1.93(−) | 1.18 | 1.10 | 1.75(−) | 1.31 | 1.69 |

TABLE 5-continued

| Racemic mixture | (+)-isomer | | | (−)-isomer | | |
|---|---|---|---|---|---|---|
| | $k_1'$ | α | Rs | $k_1'$ | α | Rs |
| 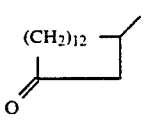 b)<br>(muscone) | | | | 0.76(−) | 1.52 | 0.91 |

Note) eluant: hexane/2-propanol = 90/10 (by volume), though the eluant used in the case marked with a symbol "b)" is hexane.

EXAMPLE 5 synthesis of cellulose tris((30)-1-phenylethylcarbamate)

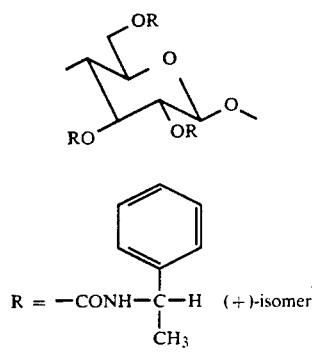

A reflux condenser was set on a 50-ml two-necked flask. 0.80 g of cellulose (Merck) and 0.90 g of LiCl were fed into the flask in a nitrogen atmosphere, followed by the addition of 7 ml of dry dimethylacetamide (on a molecular sieve). The contents were stirred under heating at 90° C. for 4 hours to give a heterogeneous system. 8 ml of dry pyridine was added to the flask, followed by the addition of (+)-1-phenylethyl isocyanate. The contents were kept at 90° C. for 27 hours to carry out a reaction. Since the resulting reaction mixture was heterogeneous, 0.80 g of (+)-1-phenylethyl isocyanate was additionally added to the flask 2 hours before the termination of the reaction. The formed polymer was precipitated in methanol and recovered with a glass filter.

amount of the obtained polymer: 2.10 g,
yield: 70.6%

The polymer was subjected to solvent fractionation with THF.
solubles: 1.96 g (91.6%)
insolubles: 0.18 g (8.4%) unreacted OH groups were recognized The amount of the obtained cellulose tris((+)-1-phenylethylcarbamate) was 1.96 g and the yield thereof was 65.9%.

| elemental analysis | C % | H % | N % |
|---|---|---|---|
| found: | 65.44 | 6.19 | 6.96 |
| calculated: | 65.72 | 6.14 | 6.97 |

APPLICATION EXAMPLE 5

0.74 g of the polymer prepared in Example 5 was dissolved in 12 ml of THF and supported on 3.00 g of silica gel (treated with 3-aminopropyltriethoxysilane). The separating agent thus obtained was packed into a column dispersed in a hexane/liquid paraffin (2:1) mixture and pressed at 330 kg/cm².

Various racemic mixtures were optically resolved by using the above separating agent (hereinafter abbreviated to "(+)-isomer". The results are given in Table 6.

TABLE 6

| Racemic mixture | (+)-isomer | | |
|---|---|---|---|
| | $k_1'$ | α | Rs |
| 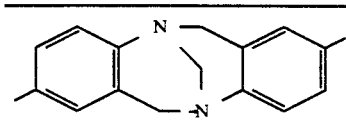 | 0.62(+) | 1.22 | |
| 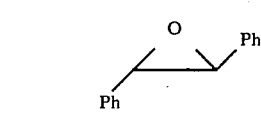 | 0.50(−) | 1.21 | 0.84 |
| 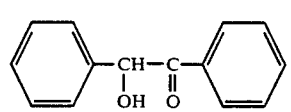 | 4.62(−) | ~1 | |
| Co(acac)₃ | 0.62(+) | ~1 | |
| 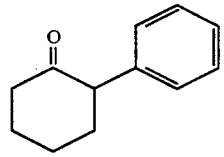 | 1.19(−) | 1.12 | 0.71 |
| 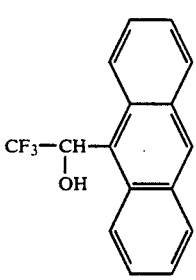 | 3.15(−) | 1.13 | |
| 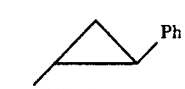 | 4.08(−) | 1.84 | 2.31 |

TABLE 6-continued

| Racemic mixture | (+)-isomer | | |
|---|---|---|---|
| | $k_1'$ | α | Rs |
| [structure: biphenyl with two OH and two CH₃ groups] | 4.55(−) | 1.32 | 1.22 |

Note) eluent: hexane/2-propanol = 90/10 (by volume)

EXAMPLE 6 synthesis of cellulose tris(1-phenylethylcarbamate)

0.80 g of cellulose (Avicel, a product of Merck) was stirred in a mixture comprising 1.2 g of LiCl and 12 ml of N,N-dimethylacetamide at 80° C. for 6 hours, followed by the addition of 6 ml of pyridine and 3.5 ml of 1-pienylethyl isocyanate. The obtained mixture was kept at 100° C. for 26 hours to carry out a reaction. The reaction mixture was poured into methanol to precipitate a product, which was recovered with a glass filter and dried in a vacuum at 60° C.

amount of the obtained product: 2.21 g
(yield: 74.2%)

The 1-phenylethyl isocyanate used above is one prepared by reacting 1-phenylethylamine with phosgene.

1-phenylethyl isocyanate: b.p.: 69° to 71° C./6 mmHg
The results of the elemental analysis of the obtained cellulose tricarbamate derivative are as follows:

| | C % | H % | N % |
|---|---|---|---|
| found: | 64.42 | 6.08 | 6.78 |
| calculated: | 65.66 | 6.18 | 6.96 |

APPLICATION EXAMPLE 6

One part (by weight, hereinafter the same applies) of the polysaccharide derivative prepared in Example 6 was dissolved in 8 parts of acetone to give a solution. This solution was mixed with 4 parts of diphenylsilane-treated silica gel (a product of Merck, Lichrospher Si-1000). The acetone was removed from the resulting mixture by vacuum distillation to give a separating agent. This agent was packed into a stainless steel column having an inner diameter of 0.46 cm and a length of 25 cm by a slurry method using methanol.

Various racemic mixtures were separated by using the packed column. The results are given in Table 7.

EXAMPLE 7

[synthesis of cellulose tris(1-(p-tolyl)ethyl carbamate)]

0.560 g of cellulose (Avicel, a product of Merck) and 0.75 g of lithium chloride were stirred in 7.5 ml of N,N-dimethylacetamide (DMA) at 80° C. for 12 hours. 4.0 ml of dry pyridine and 3.5 g of 1-(p-tolyl)ethyl isocyanate were successively added thereto to carry out a reaction at 80° C. for 48 hours. The progress of the reaction was ascertained by the presence of an absorption peak assignable to a carbamate group in the IR spectrum. The reaction mixture was poured into methanol to give a precipitate, which was recovered by filtration through a glass filter and dried. A part of the precipitate was subjected to solvent fractionation with CHCL₃ to give an objective product as a soluble part.

amount of the product: 0.86 g (38.6%)

The 1-(p-tolyl)ethyl isocyanate used above is prepared by reacting the corresponding amine with phosgene (yield: 86%, b.p.: 83.0° C./6.5 mmHg). Further, the corresponding amine is one prepared by reacting the corresponding ketone with ammonium formate (yield: 60%, b.p.: 81.0° C./13 mmHg).

The results of the elemental analysis of the obtained cellulose tricarbamate derivative are as follows:

| | C % | H % | N % |
|---|---|---|---|
| found: | 65.26 | 6.63 | 6.39 |
| calculated: | 66.96 | 6.71 | 6.51 |

APPLICATION EXAMPLE 7

A packed column was prepared by using the polymer obtained in Example 6 in a similar manner to that of Application Example 6. Various racemic mixtures were separated by using the packed column. The results are given in Table 7.

EXAMPLE 8 synthesis of cellulose tris(1-phenylpropylcarbamate)

The objective compound was prepared in the same manner as that of Example 7 except that 0.505 g of cellulose and 3.6 g of 1-phenylpropyl isocyanate were used, and that the solvent fractionation was conducted by using THF.

yield: 1.69 g (84.1%)

The 1-phenylpropyl isocyanate used above is prepared by reacting the corresponding amine with phosgene (yield: 79%, b.p.: 63.0° C./3.0 mmHg). The corresponding amine used is prepared by reacting the corresponding ketone with ammonium formate (yield 60.9%, b.p.: 47.2° C./3.0 mmHg).

The results of the elemental analysis of the obtained cellulose tricarbamate derivative are as follows:

| | C % | H % | N % |
|---|---|---|---|
| found: | 65.25 | 6.60 | 6.33 |
| calculated: | 66.96 | 6.71 | 6.51 |

APPLICATION EXAMPLE 8

A packed column was prepared by using the polymer obtained in Example 8 in a similar manner to that of Application Example 6. Racemic mixtures were separated by using the packed column. The results are given in Table 7.

EXAMPLE 9 synthesis of cellulose tris(1-(o-tolyl)ethylcarbamate

The objective compound was prepared in the same manner as that of Example 7 except that 0.510 of cellulose and 3.1 g of 1-(o-tolyl)ethyl isocyanate were used and that the solvent fractionation was carried out by using THF.

yield: 1.20 g (59.1%)

The 1-(o-tolyl)ethyl isocyanate used above is prepared by reacting the corresponding amine with phosgene (yield: 90%, b.p.: 90.2° C./12 mmHg). The corresponding amine used is prepared by reacting the corresponding ketone with ammonium formate (yield: 50%, b.p.: 59.9° C./4.5 mmHg).

The results of the elemental analysis of the obtained cellulose tricarbamate derivative are as follows:

|  | C % | H % | N % |
|---|---|---|---|
| found: | 66.33 | 6.62 | 6.50 |
| calculated: | 66.96 | 6.71 | 6.51 |

APPLICATION EXAMPLE 9

A packed column was prepared by using the polymer obtained in Example 9 in a similar manner to that of Application Example 6. Racemic mixtures were separated by using the packed column. The results are given in Table 7.

EXAMPLE 10 synthesis of amylose tris(1-phenylethylcarbamate)

A reflux condenser was set on a 50-ml two-necked flask. 0.80 g of amylose (Nakarai Chemicals) and 0.80 g of LiCl were fed into the flask in a nitrogen atmosphere, followed by the addition of 7 ml of dry dimethyacetamide (on a molecular sieve). The contents were stirred under heating at 90° C. for 5 hours to give a heterogeneous system. 10 ml of dry pyridine (on KOH) and 3.6 g of 1-phenylethyl isocyanate were successively added to the flask. The contents were kept at 90° C. for 70 hours to carry out a reaction. The resulting reaction mixture had a considerably high viscosity. When the mixture was poured into methanol, the polymer precipitated in the form of not a powder but a thread.

The polymer was subjected to solvent fractionation with THF.

solubles: 0.72 g (22.6%)

| elemental analysis | C % | H % | N % |
|---|---|---|---|
| found: | 64.39 | 6.08 | 6.80 |
| calculated: | 65.72 | 6.14 | 6.97 |

APPLICATION EXAMPLE 10

0.72 g of the polymer prepared in Example 10 was dissolved in 15 ml of THF and supported on 2.90 g of silica gel (treated with 3-aminopropyltriethoxysilane). The separating agent thus prepared was packed into a column dispersed in a hexane/liquid paraffin (2:1) mixture and pressed at 330 kg/cm².

Various racemic mixtures were optically resolved by using the packed column. The results are given in Table 8.

EXAMPLE 11 synthesis of amylose tris(1-(p-tolyl)-ethylcarbamate)

0.521 g of amylose and 0.75 g of LiCl were stirred in 7.5 ml of dry DMA at 90 C. for 5 hours, followed by the addition of 4.0 ml of dry pyridine. 3.5 g of 1-(p-tolyl)ethyl isocyanate was added to the flask to carry out a reaction at 80° C. for 24 hours. The IR spectrum revealed that unreacted OH groups remaining though the isocyanate had nearly been completely consumed. Thereafter, 1.2 g of 1-(p-tolyl)ethyl isocyanate was further added to continue the reaction for an additional 24 hours. The solvent fractionation was carried out by using THF.

yield 0.86 g (47.7%)

| elemental analysis | C % | H % | N % |
|---|---|---|---|
| found: | 65.26 | 6.63 | 6.39 |
| calculated: | 66.96 | 6.71 | 6.51 |

APPLICATION EXAMPLE 11

A packed column was prepared by using the separating agent prepared in Example 11 in a similar manner to that of Application Example 10. Various racemic mixtures were resolved by using the packed column. The results are given in Table 8.

EXAMPLE 12 synthesis of amylose tris(1-phenylpropylcarbamate)

The objective compound was prepared in the same manner as that of Example 11 except that 0.499 g of amylose and 3.6 g of 1-phenylpropyl isocyanate were used and that the solvent fractionation was carried out by using THF.

yield: 1.49 g (75.5%)

| elemental analysis | C % | H % | N % |
|---|---|---|---|
| found: | 66.09 | 6.60 | 6.44 |
| calculated: | 66.96 | 6.71 | 6.51 |

APPLICATION EXAMPLE 12

A packed column was prepared by using the polymer obtained in Example 12 in a similar manner to that of Application Example 10. Various racemic mixtures were resolved by using the packed column. The results are given in Table 8.

EXAMPLE 13 synthesis of amylose tris(1-(o-tolyl)ethylcarbamate)

The objective compound was prepared in the same manner as that of Example 11 except that 0.502 g of amylose and 3.2 g of 1-(o-tolyl)ethyl isocyanate were used, the stirring after the addition of dry DMA was conducted at 80° C. for 5 hours, followed by the addition of dry pyridine and the isocyanate, and the solvent fractionation was conducted by using THF.

yield: 1.20 g (60.0%)

| elemental analysis | C % | H % | N % |
|---|---|---|---|
| found: | 65.61 | 6.61 | 6.31 |
| calculated: | 66.96 | 6.71 | 6.51 |

APPLICATION EXAMPLE 13

A packed column was prepared by using the polymer obtained in Example 13 in a similar manner to that of Application Example 10. Various racemic mixtures were resolved by using the packed column. The results are given in Table 8.

TABLE 7

Appln. Ex. No.

TABLE 7-continued

| Racemic mixture | 6 | | | 7 | | | 8 | | | 9 | | |
|---|---|---|---|---|---|---|---|---|---|---|---|---|
| | $k_1'$ | α | Rs | $k_1'$ | α | Rs | $k_1'$ | α | Rs | $k_1'$ | α | Rs |
| 1 | — | | | 0.71(+) | 1.15 | 0.64 | — | | | — | | |
| 2 | 0.52(−)*[1] | 1.12 | | — | | | 0.58(−) | 1.09 | | 0.31(−) | 1.23 | 0.58 |
| 3 | 3.67(+) | 1.18 | 2.38 | 3.79(+) | 1.08 | | 4.73(+) | 1.22 | 3.32 | 2.71(+) | 1.25 | 2.26 |
| 4 | 0.61(+) | 1.37 | 1.25 | 1.27(+) | 1.41 | 3.20 | 0.95(+) | 1.56 | 2.69 | 0.26(+) | 1.43 | 0.62 |
| 5 | 1.19(−) | 1.09 | 0.68 | — | | | — | | | 0.82(−) | 1.07 | 0.44 |
| 6 | 3.17(−) | 1.06 | | — | | | — | | | 3.26(−) | 1.13 | 0.61 |
| 7 | 4.30(−) | 1.93 | 6.98 | 6.83(−) | 1.97 | 8.0 | 10.38(−) | 1.48 | 5.75 | 2.98(−) | 1.85 | 4.41 |
| 8 | 3.18(−) | 1.20 | 1.57 | 5.84(−) | 1.12 | 1.27 | 5.74 | 1.20 | 2.0 | 2.52(−) | 1.11 | 0.47 | separation conditions: mobile phase: n-hexane/2-propanol = 9/1, though 95/5 in Appln. Ex. 7,
flow rate: 0.5 ml/min
*[1] representing the direction of optical rotation of the first peak
The racemic mixtures 1 to 8 listed in Table 7 are as follows:

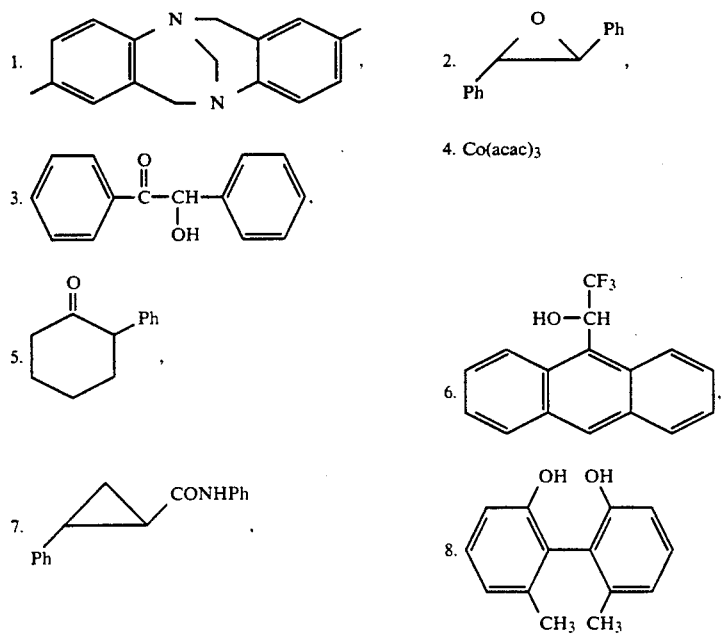

4. Co(acac)$_3$

TABLE 8

| Racemic mixture | Appln. Ex. No. | | | | | | | | | | | |
|---|---|---|---|---|---|---|---|---|---|---|---|---|
| | 10 | | | 11 | | | 12 | | | 13 | | |
| | $k_1'$ | α | Rs | $k_1'$ | α | Rs | $k_1'$ | α | Rs | $k_1'$ | α | Rs |
| 1 | 0.72(+) | 2.60 | 4.20 | 0.74(−) | 2.14 | 3.38 | 0.86(+) | 2.19 | 3.47 | 0.91(+) | 1.57 | 1.69 |
| 2 | 1.68(+) | 1.15 | 0.83 | 0.55(−) | 1.20 | 0.73 | 0.61(+) | 1.15 | 0.55 | — | | |
| 3 | 3.51(+) | 1.14 | 4.02 | 2.91(−) | 1.45 | 4.50 | 3.32(+) | 1.36 | 4.47 | 3.34(+) | 1.25 | 1.27 |
| 4 | 2.13(+) | 1.11 | 0.83 | — | | | — | | | — | | |
| 5 | 1.18(−) | 1.14 | 0.86 | 1.92(−) | 1.20 | 1.28 | 1.89(−) | 1.16 | 1.69 | 2.39(−) | 1.20 | 1.00 |
| 6 | 4.30(+) | 1.24 | 1.91 | 3.68(+) | 1.15 | 1.27 | 4.08(+) | 1.39 | 2.98 | 4.84(+) | 1.35 | 1.94 |
| 7 | 0.96(−) | 1.23 | 1.37 | 0.65(−) | 1.22 | 1.09 | 0.95(−) | 1.26 | 1.73 | 1.09(−) | 1.19 | 0.87 |
| 8 | 1.69(−) | 1.24 | 1.37 | 2.01(−) | 1.13 | 0.58 | 1.88(−) | 1.14 | 0.93 | 1.95(−) | 1.07 | | separation conditions: mobile phase: n-hexane/2-propanol = 9/1,
flow rate: 0.5 ml/min
The racemic mixtures 1 to 8 listed in Table 8 are as follows:

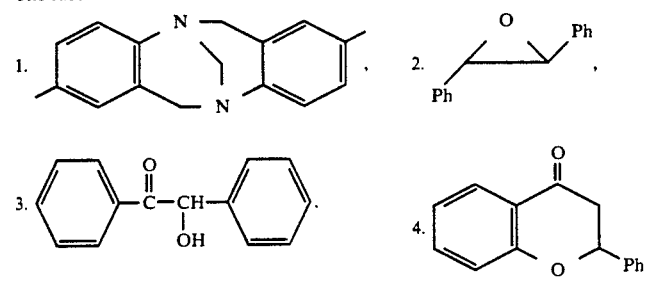

TABLE 8-continued

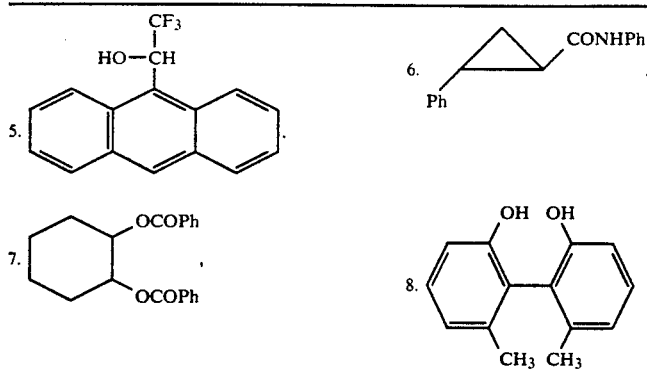

EXAMPLE 14 AND COMPARATIVE EXAMPLES 1 AND 2

The following objects of separation wee separated by using the separating agent listed in Tables 9, 10 and 11 and the results are given in Tables 9, 10 and 11.

Object of separation

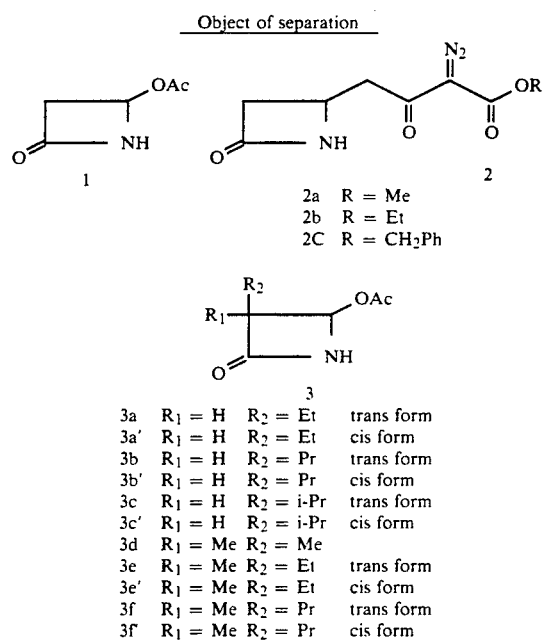

| | | | |
|---|---|---|---|
| 3a | $R_1 = H$ | $R_2 = Et$ | trans form |
| 3a' | $R_1 = H$ | $R_2 = Et$ | cis form |
| 3b | $R_1 = H$ | $R_2 = Pr$ | trans form |
| 3b' | $R_1 = H$ | $R_2 = Pr$ | cis form |
| 3c | $R_1 = H$ | $R_2 = i\text{-}Pr$ | trans form |
| 3c' | $R_1 = H$ | $R_2 = i\text{-}Pr$ | cis form |
| 3d | $R_1 = Me$ | $R_2 = Me$ | |
| 3e | $R_1 = Me$ | $R_2 = Et$ | trans form |
| 3e' | $R_1 = Me$ | $R_2 = Et$ | cis form |
| 3f | $R_1 = Me$ | $R_2 = Pr$ | trans form |
| 3f' | $R_1 = Me$ | $R_2 = Pr$ | cis form |

(wherein Ac represents an acetyl group, Me a methyl group, Et an ethyl group, Pr a propyl group, i-Pr an isopropyl group and Ph a phenyl group).

The separatory column used in Example 14 is prepared by dissolving amylose (S)-α-methylbenzylcarbamate in tetrahydrofuran to give a solution, mixing the solution with diphenylsilane-treated silica gel (a product of Merck, Lichrospher Si-1000), removing the tetrahydrofuran from the obtained mixture by vacuum distillation to give a separating agent and packing it into a stainless steel column having an inner diameter of 0.46 cm and a length of 25 cm by a slurry method with methanol. The separatory column used in Comparative Example 1 or 2 is prepared in the same manner as that described above except that cellulose 3,5-dimethylphenylcarbamate or amylose 3,5-dimethylphenylcarbamate was used.

The measurement was carried out by using a high-pressure pump TRI ROTAR-II mfd. by Japan Spectroscopic Co., Ltd. and an ultraviolet detector UV-100-III mfd. by the same company.

The capacity ratio ($k_1'$), separation factor ($\alpha$) and resolution (Rs) given in the Tables are those defined by the following equations, respectively:

$$\text{capacity ratio } (k_1') = \frac{\text{retention time of separated compound} - \text{dead time}}{\text{dead time}}$$

$$\text{separation factor } (\alpha) = \frac{\text{capacity ratio of more strongly adsorbed compound}}{\text{capacity ratio of more weakly adsorbed compound}}$$

$$\text{resolution } (Rs) = \frac{2 \times \begin{pmatrix} \text{distance between the peak of more} \\ \text{strongly adsorbed compound and that} \\ \text{of more weakly adsorbed compound} \end{pmatrix}}{\text{sum total of half-widths of both peaks}}$$

(A resolution of 1 or above means complete separation)

TABLE 9

| | Object of separation | Separating agent | Separation parameters | | | Conditions of chromatography |
|---|---|---|---|---|---|---|
| | | | $k_1'$ | $\alpha$ | Rs | |
| Ex. 14-1 | 1 | amylose (S)-α-methylbenzylcarbamate | 3.48 | 2.50 | 5.15 | hexane/ethanol = 8/2, flow rate: 1.0/min |
| 14-2 | 2a | " | 7.83 | 2.37 | 6.70 | " |
| 14-3 | 2b | " | 3.22 | 1.88 | 2.14 | " |
| 14-4 | 2c | " | 5.92 | 1.91 | 5.00 | " |
| 14-5 | 3a | " | 3.45 | 2.06 | 3.21 | " |
| 14-6 | 3a' | " | 1.79 | 9.15 | 5.84 | " |
| 14-7 | 3b | " | 3.73 | 1.99 | 5.22 | " |
| 14-8 | 3b' | " | 0.22 | 8.96 | 4.75 | " |
| 14-9 | 3c | " | 3.60 | 1.43 | 2.05 | " |
| 14-10 | 3c' | " | 0.23 | 5.78 | 8.66 | " |

TABLE 9-continued

| Object of separation | Separating agent | $k_1'$ | $\alpha$ | Rs | Conditions of chromatography |
|---|---|---|---|---|---|
| 14-11 3d | " | 1.76 | 7.56 | 6.19 | " |
| 14-12 3e | " | 2.35 | 5.02 | 4.47 | " |
| 14-13 3e' | " | 1.51 | 7.35 | 6.07 | " |
| 14-14 3f | " | 1.85 | 6.89 | 7.87 | " |
| 14-15 3f' | " | 1.29 | 4.10 | 7.65 | " |

TABLE 10

| | Object of separation | Separating agent | $k_1'$ | $\alpha$ | Rs | Conditions of chromatography |
|---|---|---|---|---|---|---|
| Comp. | 1-1 1 | Cellulose 3,5-dimethylphenylcarbamate | 4.13 | 1.12 | 0.76 | hexane/2-propanol = 9/1, flow rate: 0.5/min |
| Ex. | 1-2 2a | " | 6.80 | 1.25 | 1.73 | hexane/2-propanol = 8/2, flow rate: 0.5/min |
| | 1-3 2b | " | 4.92 | 1.16 | 1.27 | " |
| | 1-4 2c | " | 9.90 | 1.22 | 1.62 | " |
| | 1-5 3a | " | 2.00 | 1.11 | 0.96 | hexane/2-propanol = 9/1, flow rate: 0.5/min |
| | 1-6 3a' | " | 3.37 | 1.08 | 0.63 | " |
| | 1-7 3b | " | 1.82 | 1.11 | 0.76 | " |
| | 1-8 3b' | " | 3.17 | 1.12 | 1.27 | " |
| | 1-9 3c | " | 1.49 | 1.23 | 1.50 | " |
| | 1-10 3c' | " | 3.09 | 1.09 | 0.94 | " |
| | 1-11 3d | " | 1.69 | 1.13 | 0.59 | " |
| | 1-12 3e | " | 1.56 | 1.10 | — | " |
| | 1-13 3e' | " | 1.67 | 1.10 | — | " |
| | 1-14 3f | " | 1.38 | 1.00 | — | " |
| | 1-15 3f' | " | 1.40 | 1.00 | — | " |

TABLE 11

| | Object of separation | Separating agent | $k_1'$ | $\alpha$ | Rs | Conditions of chromatography |
|---|---|---|---|---|---|---|
| Comp. | 2-1 1 | amylose 3,5-dimethylphenylcarbamate | 1.54 | 1.00 | — | hexane/2-propanol = 8/2, flow rate: 0.5/min |
| Ex. | 2-2 2a | " | 7.73 | 3.14 | 4.14 | " |
| | 2-3 2b | " | 4.91 | 1.76 | 1.78 | " |
| | 2-4 2c | " | 7.00 | 1.42 | 1.94 | " |
| | 2-5 3a | " | 2.06 | 1.24 | 2.16 | hexane/2-propanol = 9/1, flow rate: 0.5/min |
| | 2-6 3a' | " | 2.30 | 1.44 | 3.55 | " |
| | 2-7 3b | " | 1.72 | 1.11 | 0.56 | " |
| | 2-8 3b' | " | 1.59 | 1.51 | 2.51 | " |
| | 2-9 3c | " | 1.52 | 1.24 | 1.29 | " |
| | 2-10 3c' | " | 2.00 | 1.40 | 2.40 | " |
| | 2-11 3d | " | 1.67 | 1.26 | 1.00 | " |
| | 2-12 3e | " | 2.06 | 1.11 | 0.72 | " |
| | 2-13 3e' | " | 1.60 | 1.00 | — | " |
| | 2-14 3f | " | 1.81 | 1.04 | — | " |
| | 2-15 3f' | " | 1.30 | 1.27 | 1.31 | " |

We claim:

1. In a process of separating a racemic mixture by passing said racemic mixture through a separating agent, the improvement comprising said separating agent comprising a polysaccharide derivative in which some or all of the hydrogen atoms of at least one group selected from among hydroxyl groups and amino groups of the polysaccharide are replaced with one or more atomic groups of the formula (1), (2) or (3):

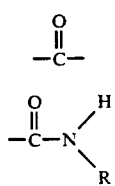

—R      (3)

wherein the number of carbon atoms constituting R is 1 to 30 and R is a group having at least one asymmetric carbon atom 2. A process as set forth in claim 1, wherein said racemic mixture is represented by the formula (4):

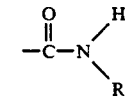

—R      (3)

wherein $R_1$, $R_2$, $R_3$ and $R_4$ are each a hydrogen atom of a substituent having 1 to 30 carbon atoms, with the proviso that if $R_1$ and $R_2$ are the same, $R_3$ and $R_4$ are different from each other and if $R_3$ and $R_4$ are the same, $R_1$ and $R_2$ are different from each other.

3. A process as set forth in claim 1, wherein at least 30 percent of said hydrogen atoms are replaced.

4. A process as set forth in claim 1, wherein at least 85 percent of said hydrogen atoms are replaced.

5. A process as set forth in claim 1, wherein said separating agent comprises said polysaccharide derivative supported on a porous carrier.

6. A process as set forth in claim 1, wherein said polysaccharide is selected from the group consisting of amylose, β-1,4-chitosan, chitin, β-1,4-mannan, β-1,4-xylan, inulin and curdlan.

7. In a process of separating a racemic mixture represented by the formula $$\underset{O}{\overset{R_2 \quad R_3}{R_1-\!\!\!\!\!\!\!\!\!\!\!\!-\!\!\!\!\!\!\!\!\!\!\!\!\!-\!\!\!\!\!\!\!\!\!\!\!\!\!R_4}}\text{NH}$$

by passing the racemic mixture through a separating agent, the improvement comprising said separating agent comprising a polysaccharide derivative of a polysaccharide selected from the group consisting of amylose, β-1,4-chitosan, chitin, β-1,4-mannan, β-1,4-xylan, inulin and curdlan, some or all of the hydrogen atoms of at least one group selected from among hydroxyl groups and amino groups of the polysaccharide being replaced with one or more atomic groups of the formula (1), (2) or (3):

$$-\overset{O}{\underset{\|}{C}}-R \tag{1}$$

$$-\overset{O}{\underset{\|}{C}}-N\overset{H}{\underset{R}{\diagdown}} \tag{2}$$

$$-R \tag{3}$$

wherein the number of carbon atoms constituting R is 1 to 30, R is a group having at least one asymmetric carbon and $R_1$, $R_2$, $R_3$ and $R_4$ are each a member selected from the group consisting of $$-CH_3, \quad -CH_2CH_3, \quad -CH_2CH_2CH_3, \quad -\underset{CH_3}{\overset{|}{CH}}-CH_3,$$

$$-CH_2-\!\!\!\bigcirc\!\!\!-, \quad -CH_2-\underset{O}{\overset{\|}{C}}-\!\!\!\bigcirc\!\!\!-, \quad -O-\underset{O}{\overset{\|}{C}}-CH_3,$$

-continued $$-\underset{CH_3}{\overset{CH_3}{\underset{|}{C}}}-\underset{O}{\overset{\|}{C}}-OCH_3, \quad -CH_2-C\equiv CH \text{ and } -CH_2C\equiv N,$$

with the proviso that if $R_1$ and $R_2$ are the same, $R_3$ and $R_4$ are different from each other and if $R_3$ and $R_4$ are the same $R_1$ and $R_2$ are different from each other.

8. In a process of separating a racemic mixture represented by the formula $$\underset{O}{\overset{R_2 \quad R_3}{R_1-\!\!\!\!\!\!\!\!\!\!\!\!-\!\!\!\!\!\!\!\!\!\!\!\!\!-\!\!\!\!\!\!\!\!\!\!\!\!\!R_4}}\text{NH}$$

wherein $R_1$, $R_2$, $R_3$ and $R_4$ are each a member selected from the group consisting of $$-CH_3, \quad -CH_2CH_3, \quad -CH_2CH_2CH_3, \quad -\underset{CH_3}{\overset{|}{CH}}-CH_3,$$

$$-CH_2-\!\!\!\bigcirc\!\!\!-, \quad -CH_2-\underset{O}{\overset{\|}{C}}-\!\!\!\bigcirc\!\!\!-, \quad -O-\underset{O}{\overset{\|}{C}}-CH_3,$$

$$-\underset{CH_3}{\overset{CH_3}{\underset{|}{C}}}-\underset{O}{\overset{\|}{C}}-OCH_3, \quad -CH_2-C\equiv CH$$

and $-CH_2-C\equiv N$, with the proviso that if $R_1$ and $R_2$ are the same, $R_3$ and $R_4$ are different from each other, and if $R_3$ and $R_4$ are the same, $R_1$ and $R_2$ are different from each other, by passing the racemic mixture through a separating agent, the improvement comprising said separating agent comprising a polysaccharide derivative in which some or all of the hydrogen atoms of at least one group selected from among hydroxyl groups and amino groups of the polysaccharide are replaced with one or more atomic groups of the formula (1), (2) or (3):

$$-\overset{O}{\underset{\|}{C}}-R \tag{1}$$

$$-\overset{O}{\underset{\|}{C}}-N\overset{H}{\underset{R}{\diagdown}} \tag{2}$$

$$-R \tag{3}$$

wherein the number of carbon atoms constituting R is 1 to 30 and R is a group having at least one asymmetric carbon atom.

* * * * *

UNITED STATES PATENT AND TRADEMARK OFFICE
CERTIFICATE OF CORRECTION

PATENT NO. : 5,202,433
DATED : April 13, 1993
INVENTOR(S) : Yoshio OKAMOTO et al It is certified that error appears in the above-identified patent and that said Letters Patent is hereby corrected as shown below:

Column 27, line 63; change the following formula:

Column 28, lines 58-69 delete in their entirety and replace with the following formula:

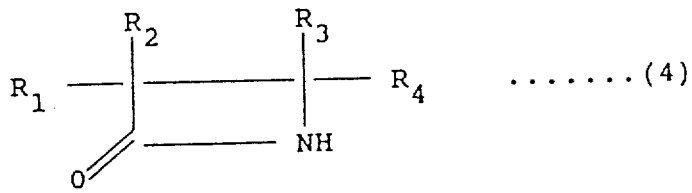

Signed and Sealed this

Fifth Day of April, 1994

*Attest:*

BRUCE LEHMAN

*Attesting Officer*   Commissioner of Patents and Trademarks